US00PP32047P3

(12) United States Plant Patent
Giacomelli et al.

(10) Patent No.: US PP32,047 P3
(45) Date of Patent: Aug. 11, 2020

(54) RASPBERRY PLANT NAMED 'ATENA'

(50) Latin Name: ***Rubus idaeus* L.**
Varietal Denomination: Atena

(71) Applicant: SANT'ORSOLA SOCIETA' COOPERATIVA AGRICOLA, Pergine Valsugana (IT)

(72) Inventors: Sara Giacomelli, Vigolo Vattaro (IT); Marco Giacomelli, Vigolo Vattaro (IT); Alessandra Viliotti, Vigolo Vattaro (IT)

(73) Assignee: SANT'ORSOLA SOCIETA' COOPERATIVA AGRICOLA, Pergine Valsugana (IT)

( * ) Notice: Subject to any disclaimer, the term of this patent is extended or adjusted under 35 U.S.C. 154(b) by 0 days.

(21) Appl. No.: 16/350,827

(22) Filed: Jan. 18, 2019

(65) Prior Publication Data

US 2019/0223340 P1 Jul. 18, 2019

(30) Foreign Application Priority Data

Jan. 18, 2018 (QZ) ..... 20180034

(51) Int. Cl.
*A01H 5/08* (2018.01)
*A01H 6/74* (2018.01)

(52) U.S. Cl.
USPC ..... Plt./204
CPC ..... *A01H 6/7499* (2018.05)

(58) Field of Classification Search
USPC ..... Plt./156, 203, 204
See application file for complete search history.

*Primary Examiner* — Susan McCormick Ewoldt
(74) *Attorney, Agent, or Firm* — Pepper Hamilton LLP

(57) ABSTRACT

A new a primocane raspberry cultivar named 'Atena' having good fruit colour and flavour, large and very firm berries is disclosed. The new cultivar has the advantages of producing fruits that are very easy to pick and produces two crops per year, where the fruits mainly ripen on current season's cane in autumn.

4 Drawing Sheets

Genus and species: *Rubus idaeus* L.
Variety denomination: 'Atena'.

BACKGROUND OF THE NEW VARIETY

A new and distinct cultivar of red raspberry (*Rubus idaeus* L.) hereinafter referred to by the cultivar denomination 'Atena' is disclosed. The new variety 'Atena' was obtained from the controlled cross between the varieties 'Dolomia Plus' (mother plant) (not patented) and 'Erika' (father plant) (U.S. Plant Pat. No. 20,841).

The crossing for the new cultivar occurred in year 2007 in Altopiano della Vigolana (Trento—Italy) and it has been subject to selection in 2008, and successively tested until 2017. The characteristics of the new cultivar have been found stable and have been transmitted without change through succeeding (more than 9 years) asexual propagations by root cutting.

Plant breeder's rights were applied for with the European Union on Jan. 18, 2018. 'Atena' has not been made publicly available.

SUMMARY OF THE INVENTION

The most outstanding and distinguishing characteristics of the cultivar 'Atena' are hereunder reported.

Primocane raspberry plant;
Good fruit colour and flavour;
Very firm light red fruits;
Easy to pick up (low adherence to plug).

The new variety produces two crops per year and the fruits mainly ripen on current season's cane in autumn.

The new variety can be propagated by: the use of suckers produced in a spawn-bed, root cutting and use of tissue culture techniques. The root cutting is to be preferred.

BRIEF DESCRIPTION OF THE PHOTOGRAPHS

The new red raspberry cultivar 'Atena' is illustrated by the accompanying photographs showing typical specimens of the new variety in colour as true as reasonably possible to make the same colour illustrations of this character by conventional photographic procedures. The photographs are of plants that are from four to six months old.

DETAILED DESCRIPTION

Figure 1:
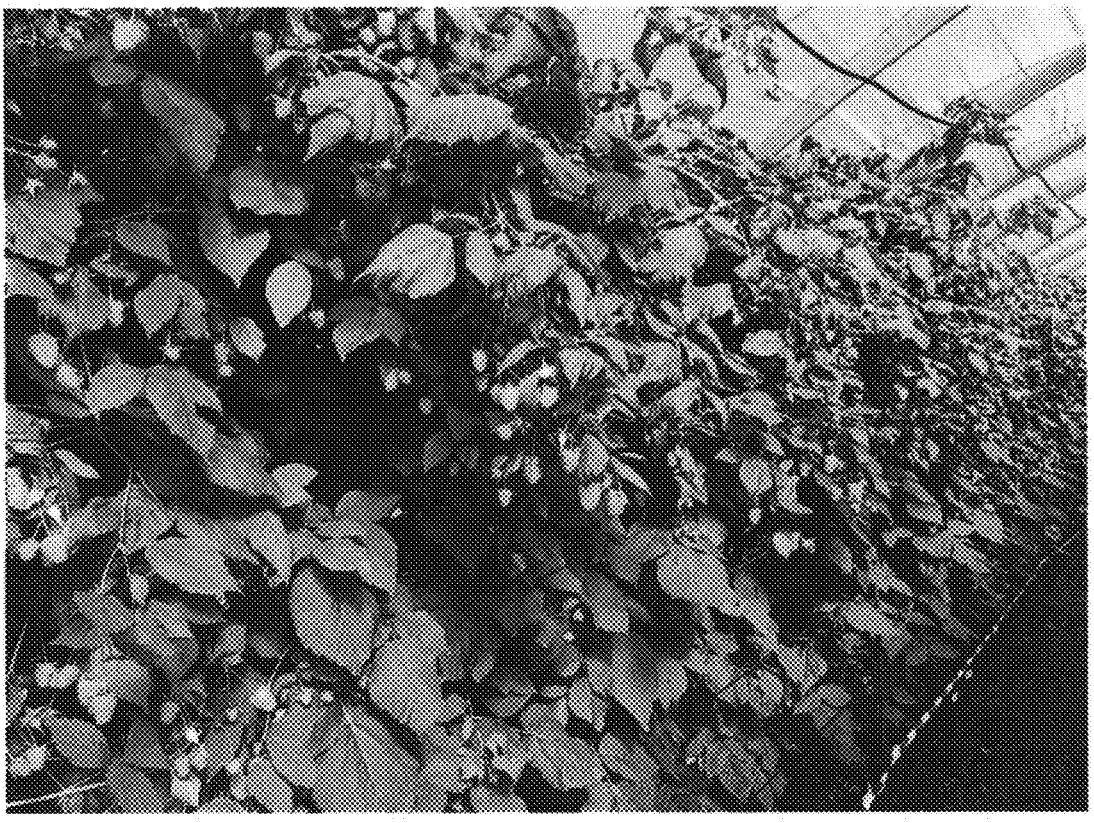
FIG. 1 is a view showing the raspberry plants with ripening fruit. The upright, tall plants and vigorous laterals can be appreciated.
Figure 2:
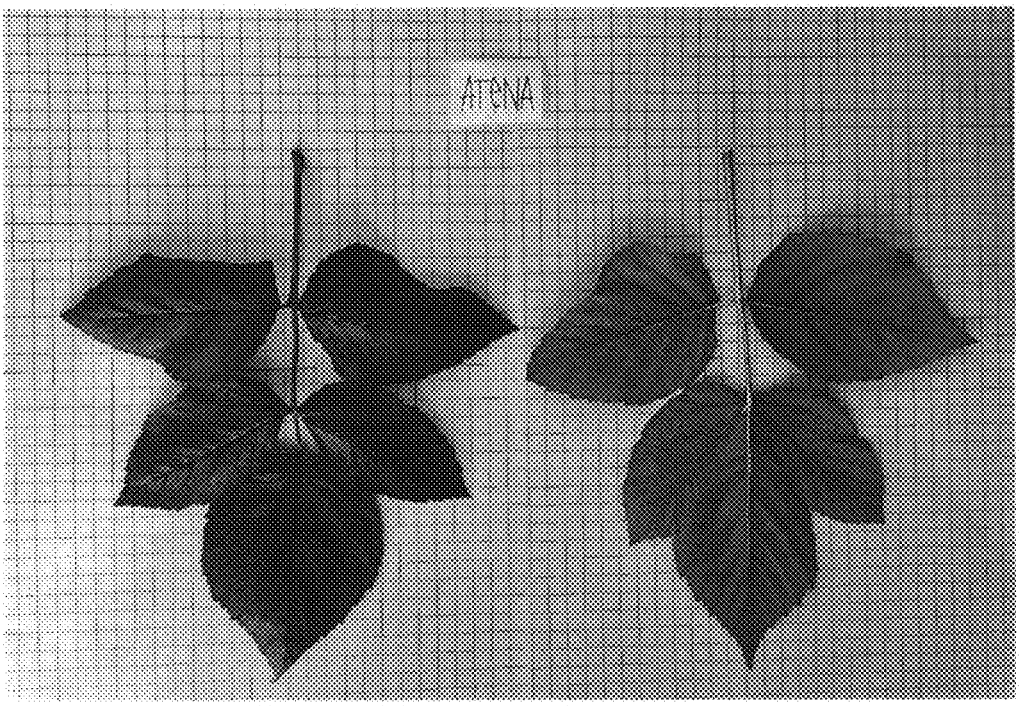
FIG. 2 is a view showing the leaf upper and lower surfaces.
Figure 3:
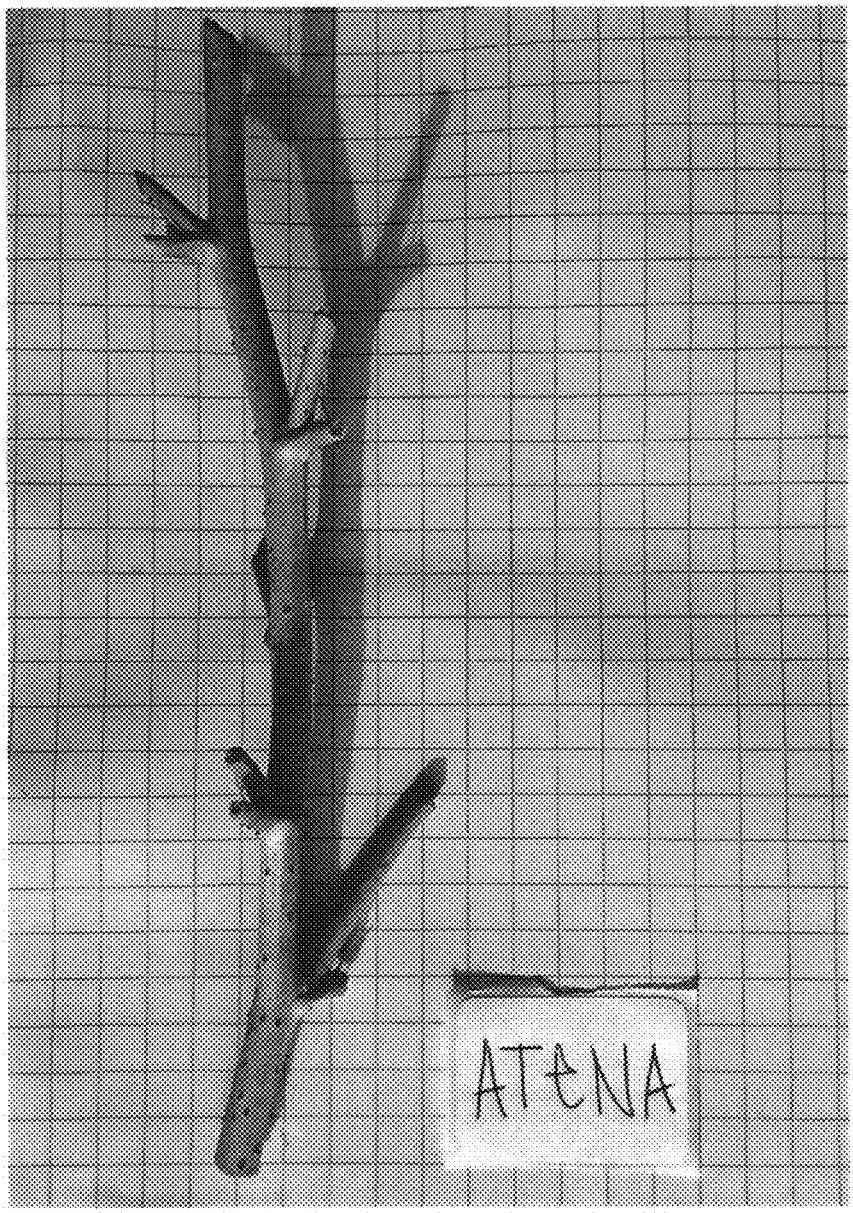
FIG. 3 is a view showing the plant primocane internode length and cane colour.
Figure 4:
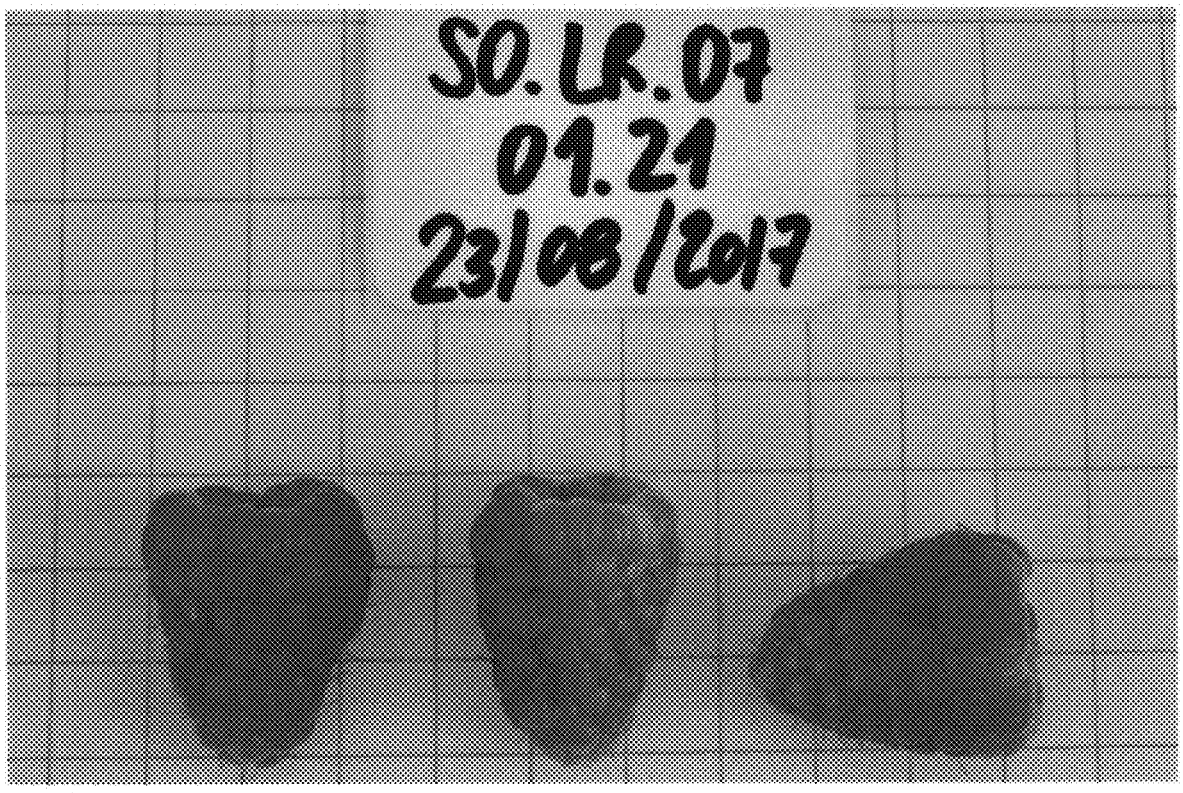
FIG. 4 is a view showing the ripe fruit size and shape.

The following detailed description set forth the distinctive characteristics of the new variety Atena. The performance of new cultivar for retention of its distinctive characteristics has been evaluated through successive asexual propagations by root cutting in the Applicant's setting in Altopiano della Vigolana, Trentino Region (Italy) under natural conditions in plastic covered high tunnels. The growing was in soils using coir as substrate.

* Colour references made to R.H.S. Colour Chart of The Royal Horticultural Society of London (Edition V)

The plant assessment was performed for 2 years. Botanical descriptions are for plants 4-6 months old.

Classification:

*Family*.—Rosaceae.

*Botanical*.—*Rubus idaeus* L.

*Common name*.—Raspberry.

Parentage: 'Dolomia Plus' x 'Erika'.

Plant:

*General habit*.—Upright canes; strong vigor; good roots system; adapted to winter conditions such as those at Altopiano della Vigolana (average min temperature 1° C.; average max temperature 5° C.); quite resilient to summer heat (average min temperature 13° C.; average max temperature 27° C.) high productivity in autumn.

*Average height* (*average*).—1.80-2 m.

*Spread* (*average*).—0.90 m.

*Shape*.—Conical.

*Vegetative bud length*.—Medium 3.0-5.0 mm.

Primocane:

*Length* (*average*).—1.80-2.0 m.

*Diameter* (*average*) *at* 1.0 *m height*.—0.8-1.0 cm.

*Texture*.—Smooth.

*Internode length* (*average*) *at* 1.0 *m height*.—6-7 cm.

*Number of fruiting laterals per cane* (*average*).—13-14.

*Number of current season's shoots*.—Few to medium.

*Young shoot colour*.—*RHS: 140A.

*Dormant cane colour*.—*RHS: 185A.

*Cane colour*.—*RHS: N144C.

*Spines*.—Present.

Spines:

*Shape*.—Conical.

*Size* (*average*).—1.0-1.5 mm.

*Density* (*average*) *at* 1.2 *m*.—3 per $cm^2$.

*Colour*.—*RHS 59A.

Foliage:

Leaves:

*Shape*.—Compound; odd-pinnate and subdivided in 3-5 ovate and doubly serrate leaflets.

*Profile in cross section*.—Concave.

*Rugosity*.—Moderate.

*Complete leaf*.—Length: 30.5 cm. Width: 19.8 cm. Number of leaflets: 3-5.

*Upper surface colour*.—*RHS 139B.

*Lower surface colour*.—*RHS 137D.

*Lateral leaflets*.—Specular.

*Lateral leaflets average size*.—Length: 11.0 cm. Width: 6.5 cm.

*Lateral leaflets apex shape*.—Pointed.

*Lateral leaflets base shape*.—Ovate.

*Lateral leaflets margin type*.—Doubly serrate.

*Terminal leaflets average size*.—Size: Length: 13.5 cm. Width: 8.3 cm.

*Terminal leaflets apex shape*.—Pointed.

*Terminal leaflets base shape*.—Ovate.

*Terminal leaflets margin type*.—Doubly serrate.

Petiole:

*Average length*.—8.7 cm.

*Average diameter*.—0.3 cm.

*Colour*.—*RHS 137D.

Inflorescence:

*Average length*.—56.5 cm.

*Average diameter*.—32 cm.

Flowers:

*Number per plant* (*average*).—250.

*Length* (*average*).—9.50 mm.

*Diameter* (*average*).—30.35 mm.

*Diameter* (*receptacle*).—8.10 mm.

*Shape*.—Pentagonal.

*Petal colour* (*upper surface*).—*RHS: NN155B.

*Petal colour* (*lower surface*).—*RHS: NN155C.

*Petal number* (*average*).—5.

*Petal shape*.—Obovate. Apex: rounded. Base: cuneate. Margin: entire.

*Sepal number* (*average*)—5. Colour (upper surface): *RHS: 142C. Colour (lower surface): *RHS: 142D. Length (average): 1.2 cm. Width (mid part): 0.5 cm.

*Fragrance*.—Absent.

*Blooming*.—July-August.

*Pedicel length* (*average*).—2.5 cm.

Fruit:

*Predominant shape*.—Elongated conical.

*Weight*.—5.5 g.

*Size*.—Length 2.7 cm. width 2.2 cm.

*Colour of ripe fruit*.—*RHS 45D.

*Colour of immature fruit*.—*RHS 41D.

*Firmness*.—Very firm (0.06 kg).

*Drupes per fruit* (*average*).—105.

*Drupe size*.—Length: 3.9 mm. Width: 3.6 mm. Depth: 5.9 mm.

*Glossiness*.—Medium.

*Adherence to plug*.—Low.

*Titratable acidity*.—31.93 meq/hg.

*Soluble solids*.—7.6° Brix.

*Yield*.—4.7 Kg/m (3 plants/m).

*Main bearing type*.—On current year's cane in autumn from half August to late October.

*Use/market*.—Suitable for consumption as high grade fresh fruit and also amenable to processing.

*Keeping quality*.—The fruit colour is stable during the storage.

*Storage capacity* (*shelf life*).—Good shelf-life.

*Shipping quality*.—Good; the attitude to storability permits shipping.

Reproductive organs:

*Pistil number per flower* (*average*).—117.

*Pistil size* (*average*).—4.41 mm.

*Stamen number per flower* (*average*).—90.

*Stamen size* (*average*).—4.82 mm.

Seeds:

*Size* (*average*).—Length: 3.41 mm. width: 2.06 mm.

*Shape*.—Kidney-shaped.

COMPARISON WITH PARENTAL AND COMMERCIAL CULTIVAR

TABLE 1

Comparison table between variety and commercial cultivar 'Evita' (U.S. Plant Pat. No. 25,695)

| Characteristic | 'Evita' | 'Atena' |
|---|---|---|
| fruit color | Orange Red | Light red |
| Plant (size/vigour) | 1.70-1.90 m | 1.80-2.00 m |
| Fruit: firmness | Firm | Very firm |
| Fruit shape | Slight irregular very elongated conical | Very regular Elongated conical |
| Fruit picking | Slight difficult | Very easy |

TABLE 2

| Comparison table with parental cultivars | | |
|---|---|---|
| Characteristic | 'Erika' (female parent) | 'Atena' |
| Fruit color | Red (RHS53A) | Strong red (RHS45D) |
| Fruit shape | Broad-conical | Elongated-conical |
| Plant vigour | Medium | Strong |
| Canes colour | Yellow Green (RHS144A) | Strong Yellowish Green (RHS144C) |
| Spines | Thin and dense | medium sparse |
| Fruit firmness | Medium firm | Very firm |

TABLE 2-continued

| Comparison table with parental cultivars | | |
|---|---|---|
| Characteristic | 'Dolomia Plus' (male parent) | 'Atena' |
| Fruit color | Strong red (RHS45A) | Strong red (RHS45D) |
| Fruit shape | Conical | Elongated-conical |
| Plant vigour | Strong | Strong |
| Canes colour | Reddish green (RHSN144A) | Strong Yellowish Green (RHS144C) |
| Spines | Thin medium dense | medium sparse |
| Fruit firmness | Firm | Very firm |

What is claimed:

1. A new and distinct cultivar of raspberry plant as substantially herein shown and described.

* * * * *